(12) United States Patent
Katsuki et al.

(10) Patent No.: US 7,879,211 B2
(45) Date of Patent: Feb. 1, 2011

(54) ANALYZING INSTRUMENT, LANCET-INTEGRATED ATTACHMENT FOR CONCENTRATION MEASURING DEVICE PROVIDED WITH ANALYZING INSTRUMENT, AND BODY FLUID SAMPLING TOOL

(75) Inventors: Koji Katsuki, Kyoto (JP); Tetsuya Sakata, Kyoto (JP); Yasuhide Kusaka, Kyoto (JP)

(73) Assignee: Arkray, Inc., Kyoto (JP)

( * ) Notice: Subject to any disclaimer, the term of this patent is extended or adjusted under 35 U.S.C. 154(b) by 39 days.

(21) Appl. No.: 10/483,443

(22) PCT Filed: Jul. 11, 2002

(86) PCT No.: PCT/JP02/07077

§ 371 (c)(1),
(2), (4) Date: Jan. 9, 2004

(87) PCT Pub. No.: WO03/006980

PCT Pub. Date: Jan. 23, 2003

(65) Prior Publication Data

US 2004/0171968 A1 Sep. 2, 2004

(30) Foreign Application Priority Data

Jul. 13, 2001 (JP) .............................. 2001-213050

(51) Int. Cl.
| | |
|---|---|
| B01J 19/12 | (2006.01) |
| C25D 17/00 | (2006.01) |
| C12M 1/00 | (2006.01) |
| C12N 9/00 | (2006.01) |
| C12N 11/00 | (2006.01) |
| C25B 9/00 | (2006.01) |
| C25B 11/00 | (2006.01) |
| C25B 13/00 | (2006.01) |
| A61B 5/00 | (2006.01) |
| A61B 17/14 | (2006.01) |
| A61B 17/32 | (2006.01) |
| B65D 81/00 | (2006.01) |
| G01N 1/00 | (2006.01) |
| G01N 27/26 | (2006.01) |
| G01N 31/00 | (2006.01) |
| G01N 33/487 | (2006.01) |

(52) U.S. Cl. .................. 204/403.01; 204/193; 204/194; 204/400; 600/583; 600/584; 606/181; 606/182; 606/184; 606/185

(58) Field of Classification Search ................ 600/584, 600/580, 573, 583; 204/193, 194, 400, 403.01; 606/181, 182, 184, 185
See application file for complete search history.

(56) References Cited

U.S. PATENT DOCUMENTS 3,419,000 A * 12/1968 Phillips ...................... 600/575
(Continued)

FOREIGN PATENT DOCUMENTS

EP  1 092 390  4/2001
(Continued)

OTHER PUBLICATIONS

Supplementary European Search Report from the corresponding EP 02 74 5986, completer Sep. 24, 2007.

*Primary Examiner*—Max Hindenburg
*Assistant Examiner*—Sean P Dougherty
(74) *Attorney, Agent, or Firm*—Hamre, Schumann, Mueller & Larson, P.C.

(57) ABSTRACT

The present invention relates to an analyzing instrument (1A) which includes a capillary (31), a fluid feed port (20) for introducing a sample liquid to the capillary (31), and a fluid feed promoter (6) for promoting the introduction of the sample liquid into the feed port (20). The capillary (31) of the analyzer (1A) may be formed on a substrate (2) for example. The fluid feed promoter (6) may include at lease one of a water-absorbing layer having a higher water-absorbing capacity than the substrate (2) and an adhesive layer having a greater adhesion to the skin than the substrate (2).

20 Claims, 7 Drawing Sheets

U.S. PATENT DOCUMENTS

| | | | |
|---|---|---|---|
| 3,623,475 A * | 11/1971 | Sanz et al. | 600/575 |
| 4,795,542 A | 1/1989 | Ross et al. | |
| 5,120,420 A * | 6/1992 | Nankai et al. | 204/403.11 |
| 5,266,179 A * | 11/1993 | Nankai et al. | 204/401 |
| 5,320,732 A * | 6/1994 | Nankai et al. | 204/403.04 |
| 5,437,999 A * | 8/1995 | Diebold et al. | 204/403.11 |
| 5,445,147 A * | 8/1995 | Schoendorfer et al. | 600/362 |
| 5,520,787 A * | 5/1996 | Hanagan et al. | 204/403.14 |
| 5,628,890 A * | 5/1997 | Carter et al. | 204/403.05 |
| 5,636,640 A | 6/1997 | Staehlin | |
| 5,735,273 A * | 4/1998 | Kurnik et al. | 600/345 |
| 5,944,662 A * | 8/1999 | Schoendorfer | 600/362 |
| 6,004,441 A * | 12/1999 | Fujiwara et al. | 204/403.14 |
| 6,071,251 A * | 6/2000 | Cunningham et al. | 600/584 |
| 6,091,975 A * | 7/2000 | Daddona et al. | 600/345 |
| 6,206,841 B1 * | 3/2001 | Cunningham et al. | 600/584 |
| 6,342,364 B1 | 1/2002 | Watanabe et al. | |
| 6,349,230 B1 * | 2/2002 | Kawanaka | 600/347 |
| 6,352,514 B1 * | 3/2002 | Douglas et al. | 600/583 |
| 6,558,320 B1 * | 5/2003 | Causey et al. | 600/300 |
| 6,562,210 B1 * | 5/2003 | Bhullar et al. | 204/403.03 |
| 6,565,738 B1 * | 5/2003 | Henning et al. | 205/777.5 |
| 6,589,260 B1 * | 7/2003 | Schmelzeisen-Redeker et al. | 606/181 |
| 6,638,772 B1 * | 10/2003 | Douglas et al. | 436/518 |
| 6,679,841 B2 * | 1/2004 | Bojan et al. | 600/309 |
| 6,706,159 B2 * | 3/2004 | Moerman et al. | 204/403.03 |
| 6,749,575 B2 * | 6/2004 | Matriano et al. | 600/564 |
| 6,766,817 B2 | 7/2004 | Da Silva | |
| 6,767,440 B1 * | 7/2004 | Bhullar et al. | 204/403.01 |
| 6,767,441 B1 * | 7/2004 | Cai et al. | 204/403.03 |
| 6,787,013 B2 * | 9/2004 | Chang et al. | 204/412 |
| 6,805,780 B1 * | 10/2004 | Ryu et al. | 204/403.01 |
| 6,830,669 B2 * | 12/2004 | Miyazaki et al. | 204/409 |
| 6,849,052 B2 * | 2/2005 | Uchigaki et al. | 600/584 |
| 6,916,410 B2 * | 7/2005 | Katsuki et al. | 204/403.05 |
| 6,923,894 B2 * | 8/2005 | Huang et al. | 204/403.06 |
| 2002/0053523 A1 | 5/2002 | Liamos et al. | |
| 2002/0099308 A1 * | 7/2002 | Bojan et al. | 600/573 |
| 2002/0179442 A1 * | 12/2002 | Miyazaki et al. | 204/403.01 |
| 2003/0196894 A1 * | 10/2003 | Cai et al. | 204/403.01 |
| 2004/0225230 A1 * | 11/2004 | Liamos et al. | 600/583 |
| 2006/0196768 A1 * | 9/2006 | Huang | 204/400 |

FOREIGN PATENT DOCUMENTS

| | | |
|---|---|---|
| EP | 1 112 717 | 7/2001 |
| EP | 1235068 A1 * | 8/2002 |
| GB | 2 236 680 | 4/1991 |
| JP | 02-95352 | 4/1990 |
| JP | 03-60645 | 3/1991 |
| JP | 09-168530 | 6/1997 |
| JP | 11-304745 | 11/1999 |
| JP | 2000-000231 | 1/2000 |
| JP | 2000-500571 | 1/2000 |
| JP | 2000-121591 | 4/2000 |
| JP | 2000-232973 | 8/2000 |
| JP | 2000-338076 | 12/2000 |
| WO | WO 97/18464 | 5/1997 |
| WO | WO 97/18465 | 5/1997 |
| WO | WO 99/30152 | 6/1999 |
| WO | WO 99/44507 | 9/1999 |
| WO | WO 00/20626 | 4/2000 |
| WO | WO 01/38862 | 5/2001 |
| WO | WO 01/72220 | 10/2001 |
| WO | WO 02/100277 | 12/2002 |

* cited by examiner

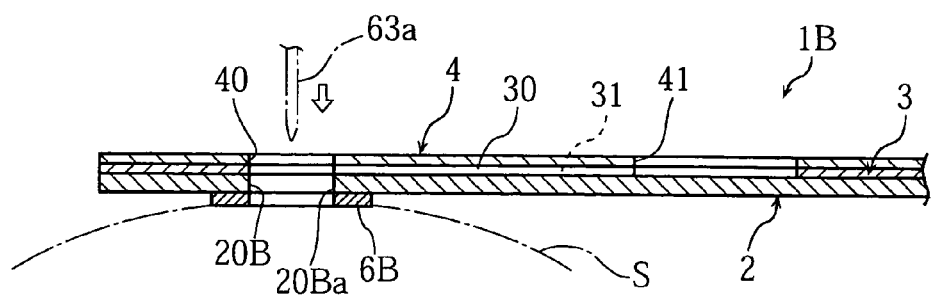
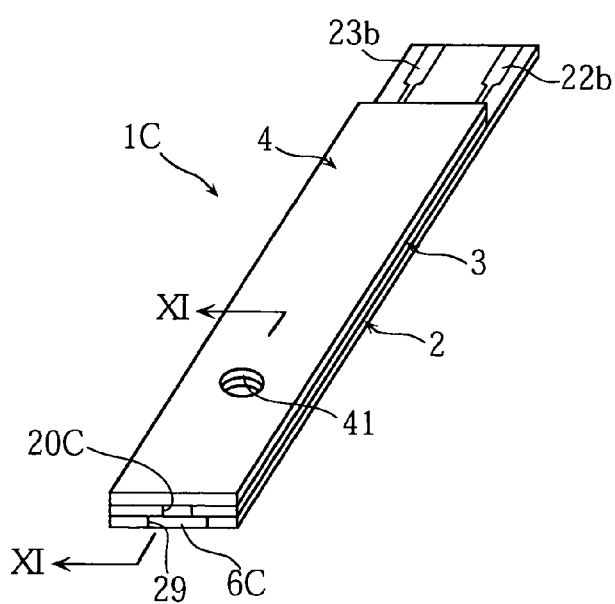
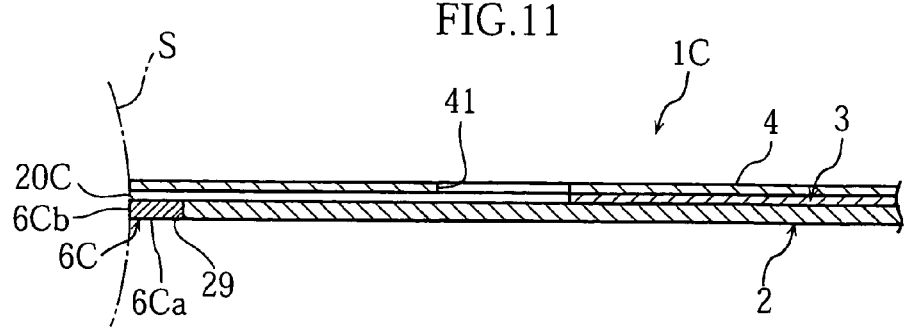

ANALYZING INSTRUMENT, LANCET-INTEGRATED ATTACHMENT FOR CONCENTRATION MEASURING DEVICE PROVIDED WITH ANALYZING INSTRUMENT, AND BODY FLUID SAMPLING TOOL

TECHNICAL FIELD

The present invention relates to an analyzing instrument used for measuring the concentration (e.g. glucose level) of a specific component in a sample liquid. The invention also relates to a lancet-integrated attachment, which, in use, is attached to a concentration measuring device, and which includes an analyzing instrument and a lancet.

BACKGROUND ART

Simple blood-sugar measuring devices have been in practical use for conveniently measuring the blood-sugar level at or away from home.

A blood-sugar measuring device is known wherein an attachment including a biosensor and a lancing needle is mounted to a tip portion of the measuring device for performing concentration measurement with respect to body fluid, as disclosed in JP-A 2000-231 for example. While a fluid feed port of the biosensor is pressed against the skin, the lancing needle of the blood-sugar measuring device is caused to protrude beyond the biosensor into the skin for bleeding. The blood bleeding from the skin is supplied to a reacting portion via a capillary of the biosensor to form a liquid phase reaction system. The blood-sugar measuring device calculates the blood-sugar level based on the value of a response current measured when a voltage is applied across the liquid phase reaction system.

However, the attachment incorporating the biosensor may fail to properly introduce blood via the sample feed port because if the skin contacts the biosensor improperly to create a gap between the biosensor and the skin, the blood may flow out along the biosensor and/or the skin via the gap. As a result, the reacting portion may fail to be supplied with an enough amount of blood needed for proper measurement.

Proposals have been made to solve the above problem by applying a water-repellent coating around the fluid feed port of the biosensor for blood leakage prevention or by arranging the feed port near the reacting portion. However, these countermeasures have turned out still insufficient for preventing blood leakage on lancing.

DISCLOSURE OF THE INVENTION

An object of the present invention is to enable concentration measurement which utilizes a capillary analyzing instrument and wherein it is possible to reliably supply the capillary with an enough amount of sample liquid needed for sample analysis.

An analyzing instrument according to a first aspect of the present invention comprises a capillary, a fluid feed port for introducing a sample liquid into the capillary, and a fluid feed promoter for promoting the introduction of the sample liquid through the fluid feed port.

The capillary of the analyzing instrument may be formed on a substrate for example. In this case, the fluid feed promoter may preferably include at least one of a water-absorbing layer having higher water-absorbing capacity than the substrate and an adhesive layer that has greater adhesion to a skin than the substrate. Further, the fluid feed promoter may preferably have higher elasticity than the substrate.

The analyzing instrument may further comprise a substrate on which a cover plate is laminated via a spacer, and a through-hole may penetrate thicknesswise through the substrate, the spacer, and the cover board. In this case, the fluid feed port may comprise the through-hole, and the fluid feed promoter may be fitted in the fluid feed port. The fluid feed promoter may be disposed around the fluid feed port. In other words, the fluid feed promoter may be preferably arranged near the fluid feed port for assisting the introduction of the sample liquid into the fluid feed port. The fluid feed promoter may preferably comprise a ring, but it may also be arcuate or otherwise shaped.

The substrate may be provided with a notch which is open at a side of the substrate for holding the body fluid feed promoter. In this case, the fluid feed port may be preferably open at said side. Again, the fluid feed promoter may include at least one of a water-absorbing layer having higher water-absorbing capacity than the substrate and an adhesive layer having greater adhesion to skin than the substrate.

A second aspect of the present invention provides a lancet-integrated attachment which comprises a lancet and an analyzing instrument for use as mounted to a concentration measuring device. The analyzing instrument comprises a capillary, a fluid feed port for introducing a sample liquid into the capillary, and a fluid feed promoter for promoting the introduction of the sample liquid through the fluid feed port.

The capillary of the analyzing instrument according to this aspect may be formed on a substrate for example. In this case, the fluid feed promoter may preferably include at least one of a water-absorbing layer having higher water-absorbing capacity than the substrate and an adhesive layer that has greater adhesion to a skin than the substrate. Further, the fluid feed promoter may have higher elasticity than the substrate.

The analyzing instrument according to this aspect may further comprise a substrate on which a cover plate is laminated via a spacer, and a through-hole may penetrate thicknesswise through the substrate, the spacer, and the cover board for allowing insertion of the lancet. In this case, the fluid feed port may comprise the through-hole, and the fluid feed promoter may be fitted in the fluid feed port. The fluid feed promoter may preferably comprise a ring. The fluid feed promoter may be disposed around the fluid feed port.

A third aspect of the present invention provides a body fluid sampling instrument which comprises a capillary, a fluid feed port for introducing body fluid into the capillary, and a fluid feed promoter for promoting the introduction of the body fluid through the fluid feed port.

The body fluid sampling instrument according to this aspect is used for sampling blood bleeding from skin. For blood sampling, the fluid feed promoter is brought into contact with a target bleeding portion of the skin The capillary of the blood sampling tool may be formed on a substrate for example. In this case, the fluid feed promoter may preferably include at least one of a water-absorbing layer having higher water-absorbing capacity than the substrate and an adhesive layer that has greater adhesion to a skin than the substrate. Further, the fluid feed promoter may preferably have higher elasticity than the substrate.

BRIEF DESCRIPTION OF THE DRAWINGS

FIG. 9 is a sectional view showing a principal part of the biosensor according to a second embodiment.

FIG. 10 is an overall perspective view of a biosensor according to a third embodiment.

FIG. 11 is a sectional view taken along lines XI-XI of FIG. 10.

BEST MODE FOR CARRYING OUT THE INVENTION

Figure 1:
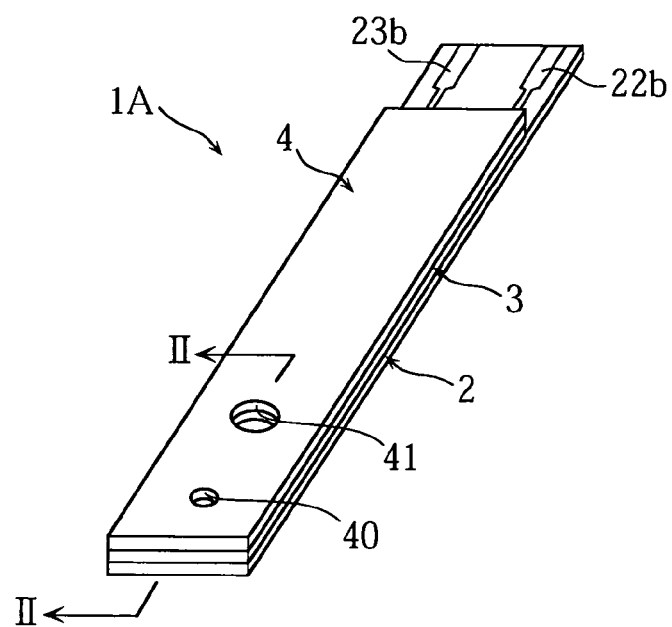
FIG. 1 is an overall perspective view of a biosensor according to a first embodiment.

An analyzer according to the present invention is described below taking a biosensor used for measuring blood-sugar level as an example.

A biosensor according to a first embodiment is described referring to FIGS. 1 through 4.

A biosensor 1A includes a substrate 2, a spacer 3, and a cover plate 4. In use, the biosensor 1A is attached to a blood-sugar measuring device 5 (refer to FIGS. 6, 7 and 8) that is described below.

The substrate 2 is rectangular and has a blood feed port 20. The blood feed port 20 is fitted with a ring 6 for helping to introduce blood.

Figure 5:
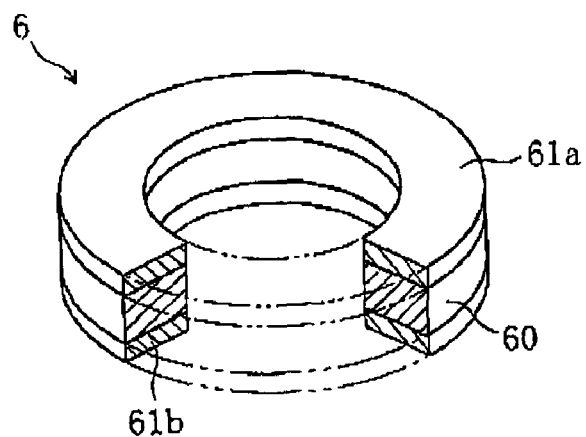
FIG. 5 is a perspective view of a ring as partially cut away.

The ring 6 has a thickness of e.g. about 70 μm which is nearly equal to the thickness of the substrate 2. As shown in FIG. 5, the ring 6 includes a water-absorbing layer 60 sandwiched between a pair of adhesive layers 61a, 61b. The water-absorbing layer 60 is a membrane which is about 50 μm in thickness formed of nonwoven fabric or the like to have a water-absorbing capacity of 2-3 g/g. The adhesive layers 61a, 61b provide suitable adhesion to the skin. The adhesive layers 61a, 61b are preferably formed of a blood-permeable material.

Figure 4:
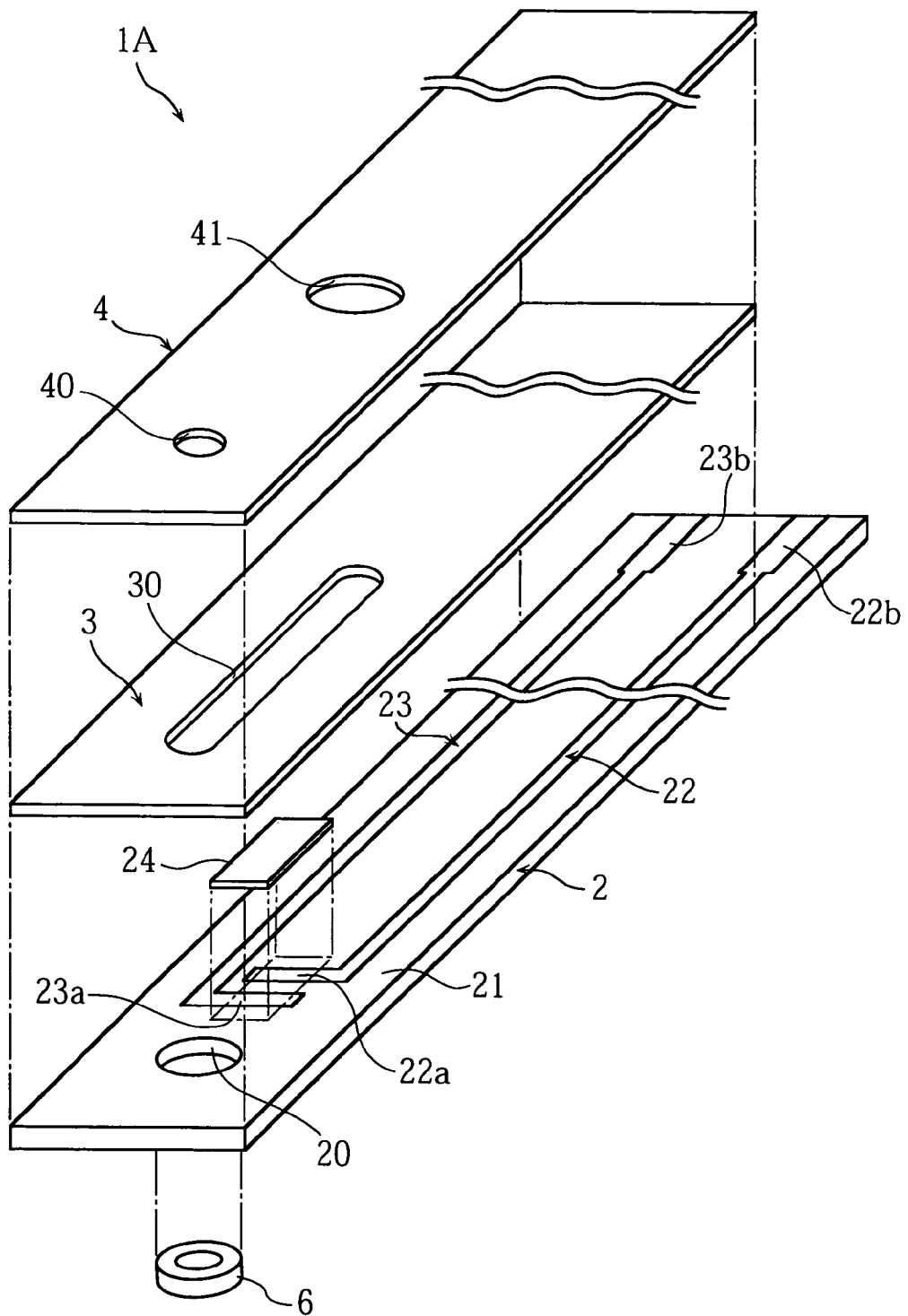
FIG. 4 is an exploded perspective view of the biosensor shown in FIG. 1.

As shown in FIG. 4, the substrate 2 has an upper surface 21 formed with a working electrode 22, a counter electrode 23, and a reacting portion 24. The working electrode 22 and the counter electrode 23 have L-bent front terminals 22a, 23a. The reacting portion 24 is a solid part containing a redox enzyme and an electron carrier for example. The redox enzyme may be glucose oxydase or glucose dehydrogenase for example. The electron carrier may be potassium ferricyanide for example.

As shown in FIGS. 1 through 4, the spacer 3 and the cover plate 4 which are laminated on the substrate 2 are rectangular but shorter than the substrate 2 for exposing the rear terminals 22b, 23b of the working electrode 22 and the counter electrode 23.

The spacer 3 is formed with a slit 30 communicating with the blood feed port 20. The slit 30 functions as a capillary 31 when the spacer 3 and the cover plate 4 are laminated on the upper surface 21 of the substrate 2. The slit 30 has an end disposed right over the blood feed port 20. The width of the slit 30 is smaller than the inner diameter of the blood feed port 20. As seen from FIGS. 2 and 5, the ring 6 is adhered to the spacer 3 via the adhesive layer 61a when fitted into the blood feed port 20. Such adhesive fixation of the ring 6 can be performed easily only by inserting the ring 6 into the blood feed port 20.

Figure 2:
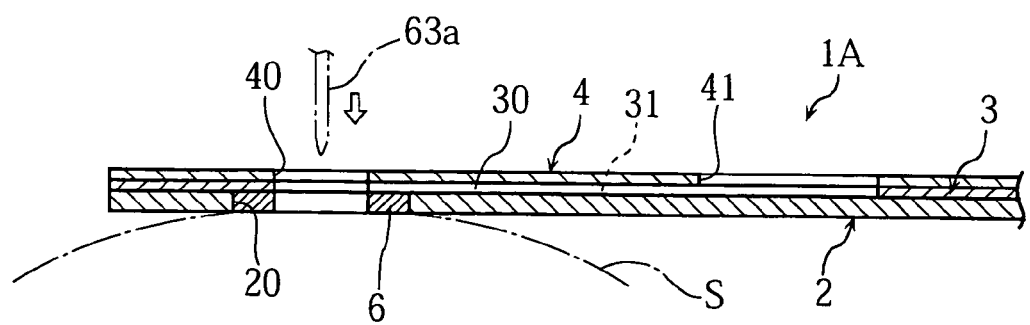
FIG. 2 is a sectional view taken along lines II-II in FIG. 1.
Figure 3:
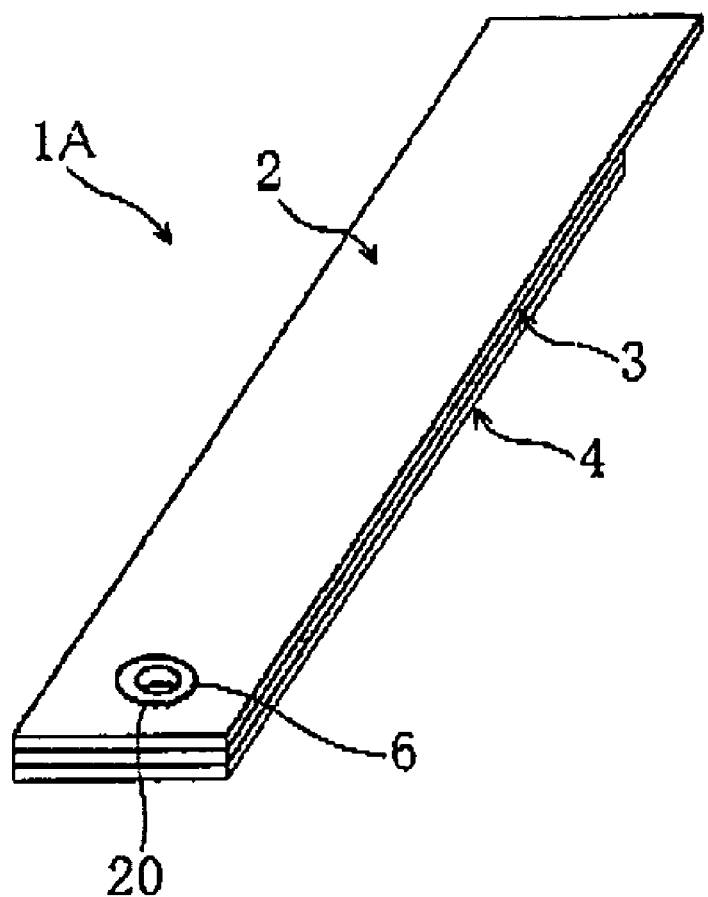
FIG. 3 is an overall perspective view of the biosensor shown in FIG. 1 as seen from the rear side.

The cover plate 4 is formed with a lancing needle insertion port 40 and an air vent hole 41. As shown in FIG. 2, the lancing needle insertion port 40 is arranged right over the blood feed port 20 for inserting a lancing needle 63a of the blood-sugar measuring device 5 (refer to FIGS. 7 and 8). Consequently, the biosensor 1A is formed with a space that extends through the substrate 2, the spacer 3, and the cover plate 4 so that the lancing needle 63a can pass through the biosensor 1A. On the other hand, the air vent hole 41 communicates with the blood feed port 20 via the capillary 31. Thus, the blood introduced from the blood feed port 20 proceeds toward the air vent hole 41 in the capillary 31 due to the capillary phenomenon. In the course of such process, the blood dissolves the reacting portion 24, whereby the redox enzyme oxidizes the glucose in the blood while reducing the electron carrier.

The biosensor 1A described above may be a part of an attachment to be mounted to a blood-sugar measuring device for use in measuring the blood-sugar level.

Figure 6:
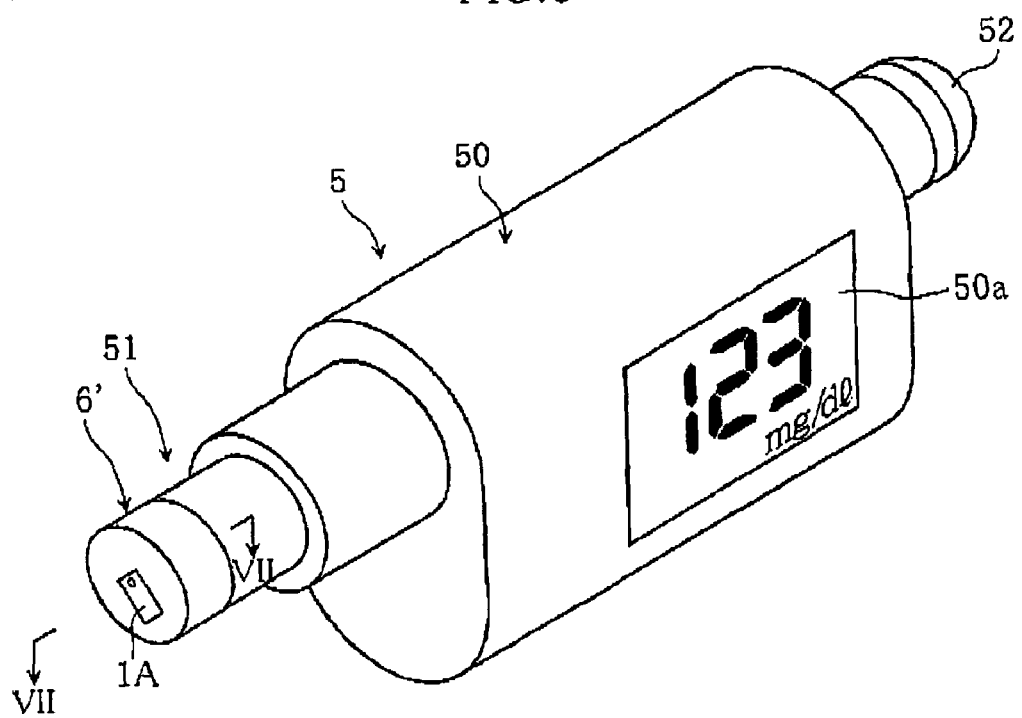
FIG. 6 is an overall perspective view of a blood-sugar measuring device.

As shown in FIG. 6, the blood-sugar measuring device 5 includes a main body 50, a mount 51, and a presser 52. The main body 50 is provided with a display 50a. The display 50a includes an LCD or the like for displaying the measurement. The mount 51, to which an attachment 6' is mounted, extends from the main body 50. The presser 52 is used for advancing the lancing needle 63a (refer to FIGS. 7 and 8).

Figure 7:
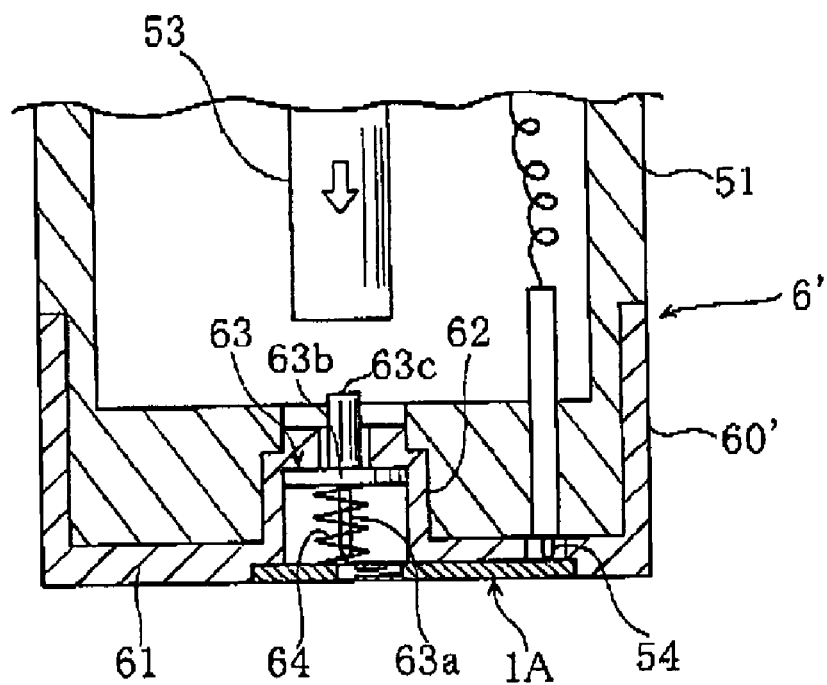
FIG. 7 is a sectional view taken along lines VII-VII of FIG. 6.

As shown in FIG. 7, the attachment 6' includes a cylinder 60' and a bottom wall 61. The cylinder 60' is fitted around the tip end of the mount 51. The bottom wall 61 is provided with an upwardly concave recess 62. The recess 62 holds a lancet 63 and has a mouth closed by the biosensor 1A that is affixed to the bottom wall 61. The lancet 63 includes, besides the lancing needle 63a, a flange 63b and a head 63c. The recess 62 receives a coil spring 64 biased between the flange 63b and the biosensor 1A.

The blood-sugar measuring device 5 is further provided with a pressing rod 53 and a pair of connector pins 54. The pressing rod 53 is driven toward the tip end of the blood-sugar measuring device by operating the presser 52. The pressing rod 53 is driven, for example, by a known latch mechanism or electromagnetic drive mechanism. The pair of connector pins 54 are connected to a non-illustrated electrical circuit while being held in contact with the rear terminals 22b, 23b of the biosensor 1 when the attachment 6' is mounted to the blood-sugar measuring device 5.

In measuring the blood-sugar level, the attachment is attached to the mount 51 of the blood-sugar measuring device 5. In this state, as shown in FIG. 2, the lancing needle 63a is disposed right over the lancing needle insertion port 40 of the biosensor 1A, while the connector pins 54 contact the rear terminals 22b, 23b of the biosensor 1A.

Next, the tip end of the blood-sugar measuring device is pressed against the skin S of an examinee so that the skin S intimately contacts the ring 6 of the biosensor 1A (refer to FIG. 2). In this state, as seen in FIGS. 2 and 5, the skin S sticks intimately to the ring 6 or the biosensor 1A due to the adhesive layer 61b at the surface of the ring 6.

Figure 8:
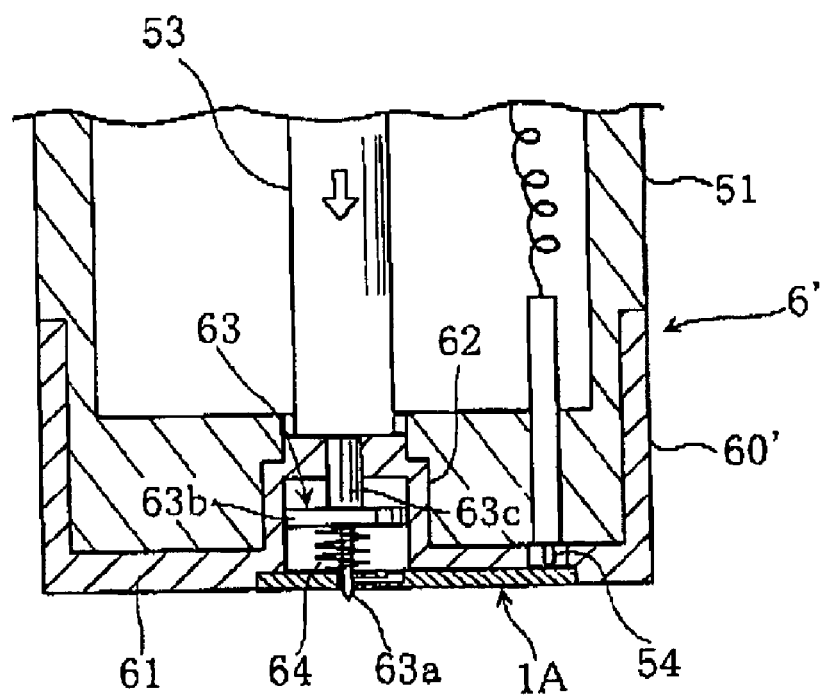
FIG. 8 is a sectional view similar to FIG. 7 with a lancet advanced to a protruding position.

Subsequently, the presser 52 is operated for lancing. As shown in FIG. 8, the operation of the presser 52 causes the pressing rod 53 to move toward the tip end of the mount 51, whereby the pressing rod 53 contacts the head 63c of the attachment 6'. As a result, the lancet 63 is pushed forward. Since the lancing needle insertion port 40, the slit 30, and the blood feed port 20 of the biosensor 1A communicate with each other to provide a penetrating path thicknesswise of the biosensor 1A, the movement of the lancet 63 causes the lancing needle 63a to pass through the biosensor 1A. As a result, the tip end of the lancing needle 63a protrudes beyond the biosensor 1A, so that the lancing needle 63a lances the skin S to promote bleeding out of the skin S. Due to the through-hole of the ring 6, the movement of the lancing needle 63a is not hindered by the ring 6 during this lancing operation even if the ring 6 is fitted in the blood feed port 20.

After the lancing operation, the pressing rod 53 of the blood-sugar measuring device 5 is preferably spaced from the lancet 63 due to the elastic force of a spring or the like. Thus, the lancet 63 returns to the position shown in FIG. 7 under the elastic force of the coil spring 64. As a result, the lancing needle 63a is prevented from pushing into the skin S for a needlessly long time, thereby reducing pain to the examinee.

When the blood from the skin S is introduced to the blood feed port 20, most of the blood is retained in the water-absorbing layer 60 of the ring 6. Since the ring 6 sticks intimately to the skin S, the blood once introduced to the blood feed port 20 is prevented from leaking outside. Further, the absorption provided by the water-absorbing layer 60 also contributes to the prevention of blood leakage from the blood feed port 20. Even if the ring 6 fails to stick intimately to the skin S while the blood is pooled temporarily in the ring 6, it is expected that the blood in a gap between the ring 6 and the Skin S is exposed to the air to clot, thereby clogging the gap. Thus, blood leakage may also be prevented in this way. On the other hand, the blood absorption provided by the water-absorbing layer 60 promotes bleeding from the skin S. As a result, enough blood for measurement can be sampled by the promotion of bleeding from the skin S as well as by the prevention of the blood leakage.

The blood introduced into the blood feed port 20 moves through the capillary 31 due to the capillary phenomenon for desolving the reacting portion 24 to create a liquid phase reaction system. The blood feed port 20 first pools an amount of blood before feeding to the capillary 31. As described above, an enough quantity of blood is retained in the biosensor 1A due to the prevention of blood leakage. Thus, an enough quantity of blood is reliably supplied to the capillary 31 and to the reacting portion 24.

A voltage is applied across the liquid phase reaction system through the connector pin 54, the working electrode 22, and the counter electrode 23. The quantity of electrons flowing between the liquid phase reaction system and the working electrode 22 is measured as an electric current at the electric circuit of the blood-sugar measuring device 5. The electric circuit determines the blood-sugar level based on the measured electric current.

Next, a biosensor according to a second embodiment is described below referring to FIG. 9. In FIG. 9, members and elements identical or similar to those in the biosensor 1A described already are given the same reference numbers, and duplicated description will be omitted.

The biosensor 1B shown in FIG. 9 includes a blood feed port 20B having an open mouth 20Ba surrounded by a ring 6B. The ring 6B includes a water-absorbing layer sandwiched between a pair of adhesive layers for example. The ring 6B may dispense with either of the water-absorbing layer and the adhesive layers.

The biosensor 1B provides the same advantages as the biosensor 1A that is previously described.

The biosensors 1A, 1B according to the first and second embodiments are not limited by the description and figures above but may be variously modified.

For example, the ring may dispense with either of the water-absorbing layer and the adhesive layers. Even in this case, blood leakage is prevented, and bleeding is promoted for reliably introducing blood into the capillary.

Further, the ring may be elastic. Due to the elasticity, the ring may provide more intimate contact with the skin when pressed against the examinee's skin, thereby preventing blood leakage more reliably. This advantage may be obtained even if dust or hairs exist between the ring and the skin.

The ring may be made elastic by adopting a highly elastic material for the water-absorbing layer and/or the adhesive layers, or by providing a highly elastic layer in addition to the water-absorbing layer and the adhesive layer. Examples of highly elastic materials include elastomers (silicone resin, acrylic resin, rubber, or the like) and gels.

The ring may be replaced with a non-perforated fluid feed promoter fitted in the blood feed port. In this case, the fluid feed promoter should have at least a needle-piercing portion which is made of a readily penetratable material or is otherwise designed to facilitate needle lancing. For example, the fluid feed promoter may include a first member provided with a through-hole and a second member to be fitted in the through-hole, or may be a sheet made from a single material. Further, the fluid feed promoter may be arcuate. Thus, the configuration and the material of the fluid feed promoter are not limitative as long as the above-described functions and advantages can be obtained.

Figure 12:
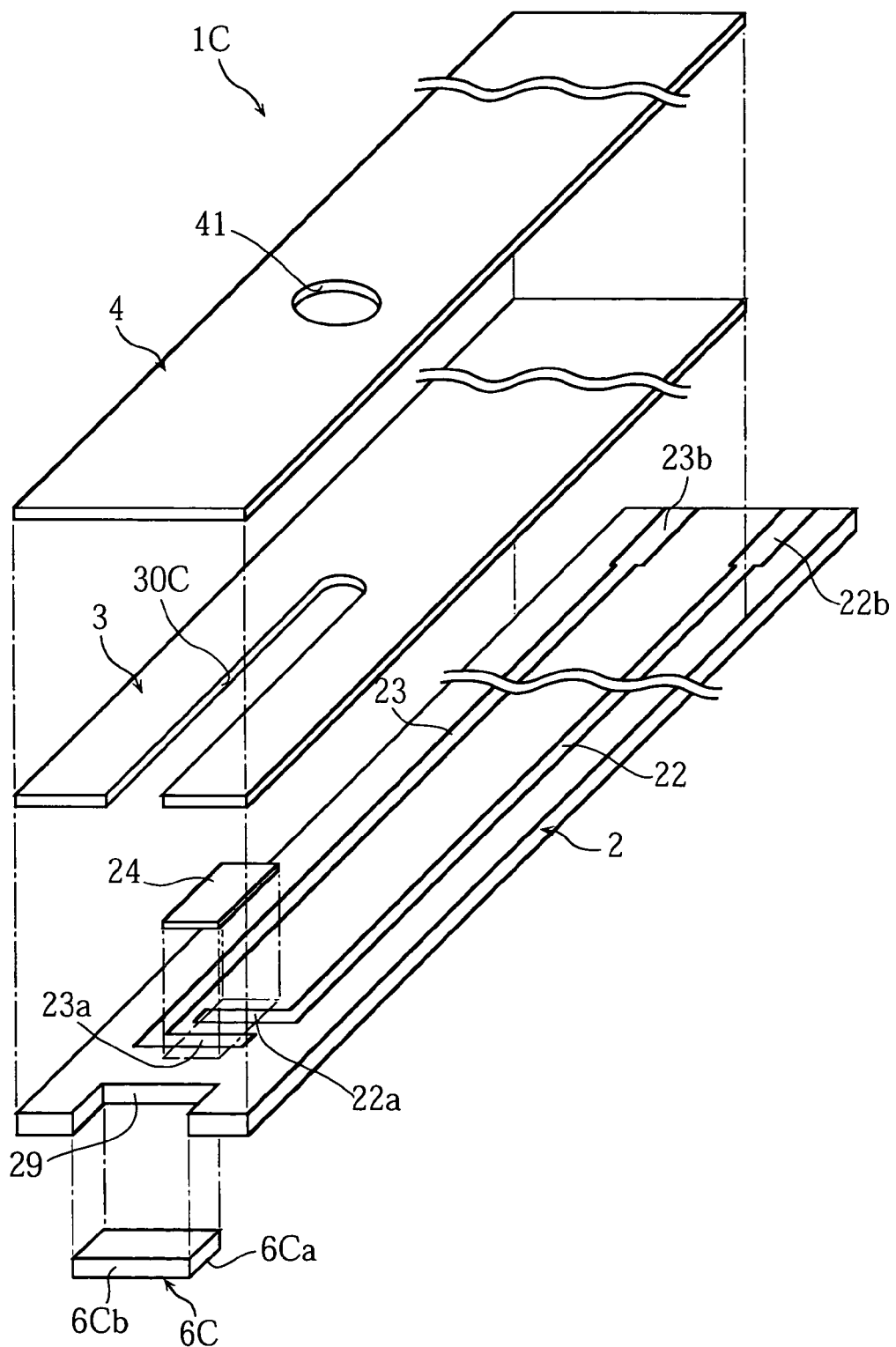
FIG. 12 is an exploded perspective view of the biosensor shown in FIG. 10.

Next, a biosensor according to a third embodiment is described referring to FIGS. 10 through 12. In these figures, members and elements identical or similar to those in the previously described biosensors are given the same reference numbers, and duplicated description will be omitted.

The biosensor 1C does not form a part of the attachment shown in FIG. 7 for mounting to the blood-sugar measuring device. Instead, the biosensor 1C is mounted alone for use in the blood-sugar measuring device.

The biosensor 1C includes a slit 30C which is open at a side to form a blood feed port 20C. As shown in FIG. 11, the thus designed biosensor 1C introduces blood when the blood feed port 20C is pressed against the bleeding skin S.

Similarly, a board 2 is formed with a notch 29 which is open at a side, and a fluid feed promoter 6C is fitted in the notch 29. The fluid feed promoter 6C has a bottom surface 6Ca and a side surface 6Cb both of which are exposed. The fluid feed promoter 6C is water-absorptive, whereas the side surface 6Cb may be adherent.

The biosensor 1C also prevents blood leakage upon blood introduction while promoting bleeding from the skin S for reliable blood introduction.

Though the first through third embodiments have been described taking a biosensor as an example in, the idea of the present invention may be also applied to a body fluid sampling tool used only for sampling body fluid (e.g. blood). An example of such a body fluid sampling tool may have the same structure as the biosensor shown in FIGS. 1 through 4 except that the working electrode 22, the counter electrode 23, and the reacting portion 24 are omitted.

The invention claimed is:

1. An analyzing instrument comprising:
   a flat cover plate having an air vent and a needle insertion port,
   a flat substrate having a fluid feed port for introducing a sample liquid, the substrate also having a reacting portion located downstream from the fluid feed port,
   a capillary formed between the substrate and the cover plate to extend from the fluid feed port and the needle insertion port toward the air vent for transporting the sample liquid to the reacting portion, and a fluid absorber fitted entirely within the fluid feed port of the substrate upstream from the capillary, the fluid absorber having a needle insertion opening, wherein the needle insertion opening of the fluid absorber is aligned with the needle insertion port of the cover plate for allowing insertion of a lancing needle through the needle insertion opening of the fluid absorber, the capillary and the needle insertion port of the cover plate.

2. The analyzing instrument according to claim 1, wherein the fluid absorber includes a water-absorbing layer having higher water-absorbing capacity than the substrate.

3. The analyzing instrument according to claim 1, wherein the fluid absorber includes an adhesive layer having greater adhesion to the skin than the adhesion that the substrate has to the skin.

4. The analyzing instrument according to claim 1, wherein the fluid absorber has higher elasticity than the substrate.

5. The analyzing instrument according to claim 1, further comprising a spacer interposed between the substrate and the cover plate, wherein the spacer is formed with a through-hole aligned with the liquid feed port of the substrate and the needle insertion opening of the cover plate.

6. The analyzing instrument according to claim 1, wherein the fluid absorber has a thickness equal to a thickness of the substrate.

7. The analyzing instrument according to claim 6, wherein the fluid absorber comprises a ring.

8. The analyzing instrument according to claim 1, wherein the fluid absorber is disposed around the fluid feed port.

9. A lancet-integrated attachment for mounting to a concentration measuring device, the attachment comprising a lancet and an analyzing instrument, wherein the analyzing instrument comprises a flat cover plate having an air vent and a needle insertion port, a flat substrate having a fluid feed port for introducing a sample liquid, the substrate also having a reacting portion located downstream from the fluid feed port, a capillary formed between the substrate and the cover plate to extend from the fluid feed port and the needle insertion port toward the air vent for transporting the sample liquid to the reacting portion, and a fluid absorber fitted entirely within the fluid feed port of the substrate upstream from the capillary, the fluid absorber having a needle insertion opening, wherein the needle insertion opening of the fluid absorber is aligned with the needle insertion port of the cover plate for allowing insertion of the lancet through the needle insertion opening of the fluid absorber, the capillary and the needle insertion port of the cover plate.

10. The lancet-integrated attachment according to claim 9, wherein the fluid absorber includes at least one of a water-absorbing layer having higher water-absorbing capacity than the substrate and an adhesive layer having greater adhesion to the skin than the adhesion that the substrate has to the skin.

11. The lancet-integrated attachment according to claim 10, further comprising a spacer interposed between the substrate and the cover plate, wherein the spacer is formed with a through-hole aligned with the liquid feed port of the substrate and the needle insertion opening of the cover plate for allowing insertion of the lancet.

12. The lancet-integrated attachment according to claim 9, wherein the fluid absorber comprises a ring.

13. The lancet-integrated attachment according to claim 9, further comprising a cylindrical housing for fitting on a mount portion of the concentration measuring device, and a bottom wall formed at one end of the cylindrical housing for supporting the analyzing instrument, the bottom wall including an upwardly concave recess for movably accommodating the lancet.

14. The lancet-integrated attachment according to claim 13, wherein the upwardly concave recess is defined by a cylindrical side wall and a top wall, the lancet including a flange slidably guided by the cylindrical side wall of the upwardly concave recess, a head projecting from the flange through the top wall of the upwardly concave recess, and a lancing needle projecting from the flange toward the analyzing instrument.

15. The lancet-integrated attachment according to claim 14, further comprising a spring interposed between the flange of the lancet and the analyzing instrument for urging the flange toward the top wall of the upwardly concave recess.

16. The lancet-integrated attachment according to claim 14, wherein the bottom wall of the cylindrical housing is formed with a downwardly open cutout for receiving the analyzing instrument.

17. A body fluid sampling instrument comprising:
a flat cover plate having an air vent and a needle insertion port,
a flat substrate having a fluid feed port for introducing body fluid, the substrate also having a reacting portion located downstream from the fluid feed port,
a capillary formed between the substrate and the cover plate to extend from the fluid feed port and the needle insertion port toward the air vent for transporting the body fluid to the reacting portion, and
a fluid absorber fitted entirely within the fluid feed port of the substrate upstream from the capillary, the fluid absorber having a needle insertion opening, wherein the needle insertion opening of the fluid absorber is aligned with the needle insertion port of the cover plate for allowing insertion of a lancing needle through the needle insertion opening of the fluid absorber, the capillary and the needle insertion port of the cover plate.

18. The body fluid sampling instrument according to claim 17, which is used for sampling blood bleeding from the skin, wherein the fluid absorber is brought into contact with a target bleeding portion of the skin for blood sampling.

19. An analyzing instrument comprising:
a flat cover plate having an air vent and a needle insertion port,
a flat substrate having a fluid feed port for introducing a sample liquid, the substrate also having a reacting portion located downstream from the fluid feed port,
a capillary formed between the substrate and the cover plate to extend from the fluid feed port and the needle insertion port toward the air vent for transporting the sample liquid to the reacting portion, and
a fluid absorber provided upstream from the capillary, the fluid absorber having a needle insertion opening,
wherein the needle insertion opening of the fluid absorber is aligned with the needle insertion port of the cover plate for allowing insertion of a lancing needle through the needle insertion opening of the fluid absorber, the capillary and the needle insertion port of the cover plate, and
wherein the fluid absorber is fitted within the fluid feed port of the substrate, the fluid absorber including a skin-contacting surface flush with a surface of the substrate facing away from the cover plate.

20. An analyzing instrument comprising:
a flat cover plate having an air vent and a needle insertion port,
a flat substrate having a fluid feed port for introducing a sample liquid, the substrate also having a reacting portion located downstream from the fluid feed port, a capillary formed between the substrate and the cover plate to extend from the fluid feed port and the needle insertion port toward the air vent for transporting the sample liquid to the reacting portion, and a fluid absorber provided upstream from the capillary, the fluid absorber having a needle insertion opening, wherein the needle insertion opening of the fluid absorber is aligned with the needle insertion port of the cover plate for allowing insertion of a lancing needle through the needle insertion opening of the fluid absorber, the capillary and the needle insertion port of the cover plate, and wherein the fluid absorber is disposed around the fluid feed port on a surface of the substrate facing away from the cover plate.

* * * * *